United States Patent [19]

Jagielinski

[11] Patent Number: 5,574,363
[45] Date of Patent: Nov. 12, 1996

[54] STABILITY METHOD AND APPARATUS FOR NONDESTRUCTIVE MEASURE OF MAGNETIC SATURATION FLUX DENSITY IN MAGNETIC MATERIALS

[75] Inventor: Tomasz M. Jagielinski, Carlsbad, Calif.

[73] Assignee: Eastman Kodak Company, Rochester, N.Y.

[21] Appl. No.: 196,052

[22] Filed: Feb. 14, 1994

[51] Int. Cl.⁶ .......................... G01N 27/74; G01R 33/12
[52] U.S. Cl. .......................... 324/204; 73/53.01; 73/61.42
[58] Field of Search .................................. 324/204, 201, 324/202, 214, 228, 233, 239–243, 226, 262, 71.4; 73/861.08, 861.11, 861.13–861.16, 53.01, 61.42; 340/627, 631

[56] References Cited

U.S. PATENT DOCUMENTS

| 3,777,561 | 12/1973 | Lewis | 73/861.13 |
|---|---|---|---|
| 4,522,501 | 6/1985 | Shannon | 366/142 |
| 4,651,092 | 3/1987 | Brunsch et al. | 324/204 |
| 4,808,922 | 2/1989 | Eder et al. | 324/204 |
| 5,089,781 | 2/1992 | Arichika et al. | 324/204 X |
| 5,287,056 | 2/1994 | Jackson et al. | 324/239 |

FOREIGN PATENT DOCUMENTS

| 0970288 | 10/1982 | U.S.S.R. | 324/204 |
|---|---|---|---|
| 0995035 | 2/1983 | U.S.S.R. | 324/204 |
| 1126859 | 11/1984 | U.S.S.R. | 324/204 |
| 1383239 | 3/1988 | U.S.S.R. | 324/204 |

Primary Examiner—Sandra L. O'Shea
Assistant Examiner—Jay M. Patidar
Attorney, Agent, or Firm—William F. Noval

[57] ABSTRACT

In order to measure the magnetic saturation flux density of a sample material, a first and a second sample holder are symmetrically positioned on the same side of a cylindrical permanent magnet. Coils are placed around the sample holders and the cylindrical permanent magnet is rotated. The signals induced in the coils in the absence of a magnetic material in one of the sample holders are applied to an amplifier in such a manner as to provide a null input signal. When a sample is placed in one of the sample holders, the magnetic saturation flux density can be measured. The present device finds particular application to determining the concentration of a magnetic particles dispersed in a (coating) fluid. The fluid can flow through a sample holder for measurement. In addition, a reference fluid can flow through the second sample holder for better process control. The geometry of the sample holder carrying a fluid material is specified to increase the accuracy of the measurements.

17 Claims, 2 Drawing Sheets

STABILITY METHOD AND APPARATUS FOR NONDESTRUCTIVE MEASURE OF MAGNETIC SATURATION FLUX DENSITY IN MAGNETIC MATERIALS

RELATED APPLICATION

U.S. patent application Ser. No. 169,082 entitled APPARATUS AND METHOD FOR A B-H METER USING A ROTATING MAGNETIC FIELD, filed on Dec. 17, 1993 in the name of Frederick J. Jeffers and assigned to the assignee of the present application is a related application.

FIELD OF THE INVENTION

This invention relates generally to the measurement of magnetic properties and, more particularly, to the measurement of magnetic properties in a material having magnetic particles dispersed therein.

BACKGROUND OF THE INVENTION

In a non-magnetic medium, such as a fluid, in which magnetic particles are dispersed, a measurement of the magnetic properties has been used to determine parameters, such as the magnetic particle concentration, in the medium. In the prior art, the response of the medium to the application of a magnetic field to a fluid has been used to measure the properties of magnetic particles suspended therein and, consequently, to determine the properties of fluid itself. In U.S. Pat. No. 4,651,092, entitled METHOD OF DETERMINING DISPERSION OF VISCOSITY OF RESIN/SOLVENT MIXTURE CONTAINING MAGNETIC PARTICLES, issued on Mar. 17, 1987 in the name of A. Brunsch et al., a magnetic field generated by a set of coils is applied to fluid to determine characteristics of magnetic particles suspended in a fluid medium, for example, the concentration of magnetic particles in the medium. In the configuration disclosed, a relatively small magnetic field (approximately 10 Oe) is generated and applied to the material under test. In U.S. Pat. No. 4,522,501, entitled MONITORING MAGNETICALLY PERMEABLE PARTICLES IN ADMIXTURE WITH A FLUID CARRIER, issued on Jun. 11, 1985 in the name of M. A. Shannon, the concentration of magnetic particles in a fluid medium is determined by measuring the change in torque in a rotating conducting member resulting from the eddy current variation when the fluid medium is used to shield the rotating member from an applied magnetic field. Neither of the references provides the requisite accuracy for the determination of the magnetic properties of the magnetic medium.

Apparatus is commercially available for measuring the magnetic properties of a material. For example, Model 7600A BH Meter available from LDJ Incorporated is a microprocessor-controlled device for the measurement of magnetic properties of materials. Such devices are expensive and typically can measure parameters which, in many situations are not important for characterization of the material.

A need has therefore been felt for apparatus and an associated method for measuring the dispersion or the magnetic saturation of a fluid having magnetic particles suspended therein; apparatus which is relatively simple, accurate, and which does not involve undue complexity.

SUMMARY OF THE INVENTION

The present invention is directed to overcoming one or more of the problems set forth above. Briefly summarized, according to one aspect of the present invention, a cylindrical permanent magnet which is caused to physically rotate, has a sample coil and a reference coil symmetrically disposed, side-by-side with respect to the cylindrical magnet. The sample coil surrounds a sample holder in which a material sample can be placed. Similarly, the reference coil includes a reference sample holder. The reference coil and the sample coil, in the absence of a magnetic material interacting with the rotating (and changing) field, can be adjusted to provide a null signal when applied to the input terminals of an amplifier/meter. When a material sample is placed in the material sample holder, the magnetic particles of the sample material interacts with the changing magnetic field resulting from the rotation of the permanent magnet. A voltage is generated as a result of the interaction of the medium sample with the changing magnetic field. The voltage can be used to determine the saturation flux of the material and, consequently, the concentration of magnetic particles. By flowing a fluid material sample through the sample holder, the apparatus can be used in process control system. A reference fluid material, a material which has the desired magnetic properties, can flow through the reference sample holder and be used to provide a null signal when the magnetic properties of the material sample are the same as the magnetic properties of the reference material. The sample holders can have a rectangular cross-section.

The present invention advantageously provides for an accurate saturation flux measurement without the use of elaborate apparatus. In particular, the apparatus can be used to determine the concentration of magnetic particles. The disclosed configuration is suitable for use with a fluid medium in a process control system.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 3A is an end view of one of possible shape of the sample holders for the sample material and/or for the reference material, while

DETAILED DESCRIPTION OF THE INVENTION

Figure 1:
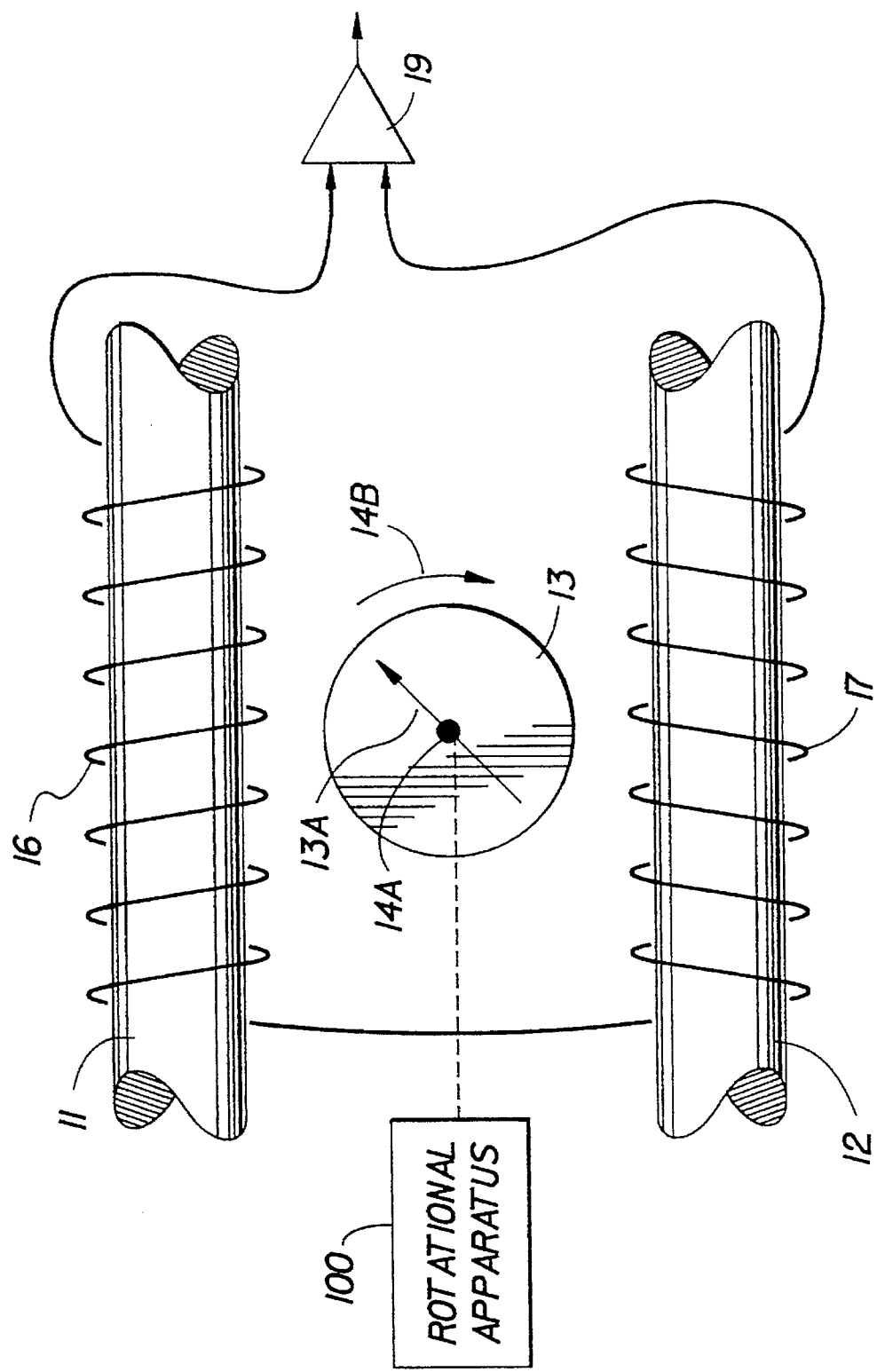
FIG. 1 is a schematic block diagram of the configuration used in determining the magnetic properties of a sample of magnetic material using two coils symmetrically positioned on opposite sides of the permanent magnet.

Referring to FIG. 1, a cylindrical permanent magnet 13 has an axis of magnetization in a direction perpendicular to the cylindrical axis as indicated by the arrow 13A. The cylindrical permanent magnet 13 is rotated by apparatus 100 about an axis 14A in a direction indicated by the arrow 14B.

Sample holders 11 and 12 are symmetrically positioned with respect to the cylindrical permanent magnet 13 on opposite sides of the magnet. Each sample holder has an axis positioned in a plane perpendicular to the axis of rotation 14A. Sample holder 11 has coil 16 wrapped therearound, while sample holder 12 has coil 17 wrapped therearound. The coils 16 and 17 are coupled so that voltages induced therein by the changing magnetic field (i.e., from rotating cylindrical permanent magnet 13) are in opposition. The coils 16 and 17 are coupled in series and applied to input terminals of amplifier 19. Typically, the coils 16 and 17 are arranged so that, in the absence of a sample material, no voltage signal is applied to the input terminals of amplifier/meter 19.

When a magnetic material is placed in one of the sample holders 11 and 12, the (changing) magnetic field from the rotating cylindrical permanent magnet 13 causes the magnetic material to generate a (changing) magnetic field. The changing magnetic field induces a voltage in the associated coil which is not duplicated in the other coil. Consequently, the signals induced in the coils 16 and 17 are no longer balanced and a voltage is present on the input terminals of amplifier/meter 19.

In the preferred embodiment, the rotating magnet B-H meter is used to measure the pigment concentration or saturation magnetization of a coating material. The magnet is 1.5 inches in diameter by 2.0 inches long and is fabricated from an NdFeB material. The magnet has a field of approximately 2400 Oe which is selected to insure saturation of the 900 Oe coercivity particles in the coating material. A ⅛ horsepower motor rotates the permanent magnet at 3,000 RPM so that the field frequency is 50 Hz. The windings have 1,000 turns. With no sample material in the device, the primary voltages induced in the coils will cancel. In operation, the coating material will be placed in the sample holder associated with one of the coils. The magnetic field from the permanent magnet will magnetize the coating material and the voltage induced in the coil will be proportional to the time rate of change of the magnetic field. Electronic integration can give the saturation flux density of the coating material. Calibration can be performed by inserting a standard material into the second sample holder. In the operation of the invention, the saturation flux density of the coated film is about 45 gauss. The saturation flux density of the coating material can be ⅓ less or 15 gauss. Using a nominal tube diameter of 1 cm., a magnetic flux of approximately 12 Maxwells will be produced. This magnetic flux is approximately a factor of 30 greater than the minimum magnetic flux that can be measured conveniently in the commercially available B-H meters. Therefore, the signal-to-noise ratio should not be a problem with the present invention.

Figure 2:
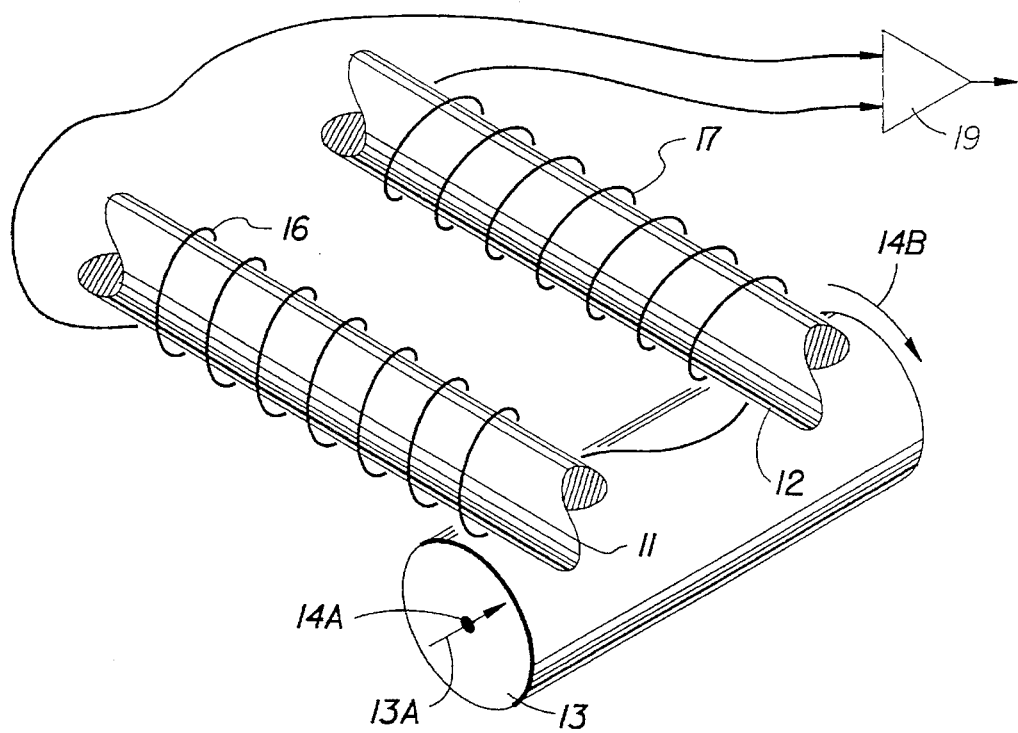
FIG. 2 is a schematic block diagram of the of the configuration used in determining the magnetic properties of a sample of magnetic material having coils positioned side-by-side and proximate to a cylindrical permanent magnet according to the present invention.

Referring to FIG. 2, a perspective view of the apparatus of the present invention wherein the sample holder 11 and the sample holder 12 are positioned on the same side of the cylindrical magnet is shown. This configuration for the sample holders eliminates the effects of non-concentricity of the permanent magnet, i.e., uncontrolled variation in the magnetic field amplitude for each position of the sample holder. The reference sample holder can have material flowing therethrough having the preselected magnetic properties. The amplifier/meter 19 can provide an error signal which is used to control the properties of the material undergoing the testing procedure.

Figure 3A:
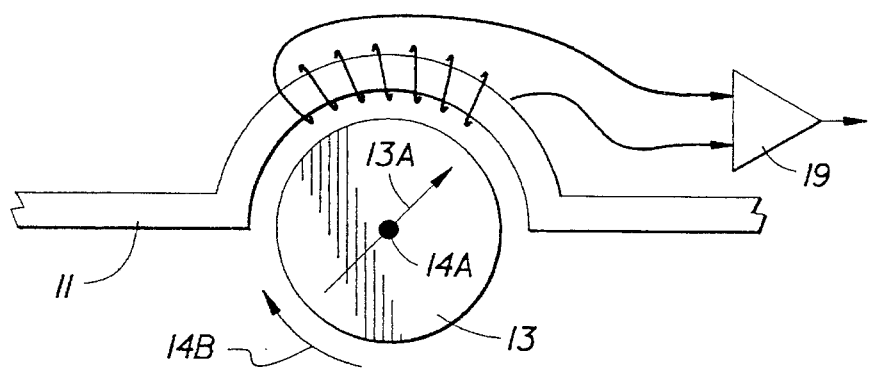
Figure 3B:
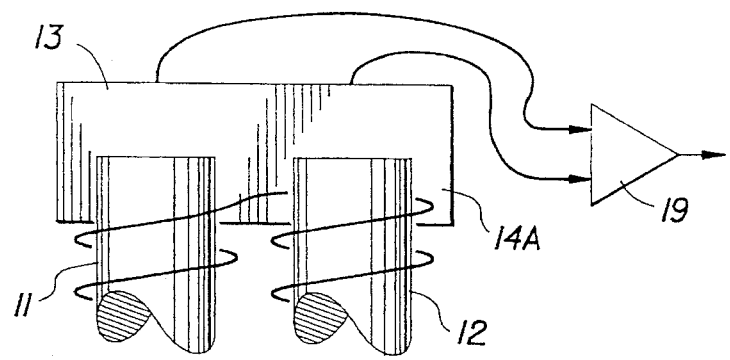
FIG. 3B is a frontal view of the medium and reference sample holders according to the present invention.

Referring to FIG. 3A, an end view of the configuration of the rotating magnet B-H meter is shown. This view illustrates that the configuration of the sample holders 11 (shown) and 12 (not shown), are formed and positioned in such a manner as to remain a uniform distance from the axis of the cylindrical permanent magnet, the entering and the exiting portions of the sample holders being parallel to the maximum magnetic field experienced by the materials entering and exiting through the sample holders. Other configurations for the sample holders, such as the configuration shown in FIG. 2 can be employed, the important feature being that both sample holders are positioned on the same side of the rotating magnet. FIG. 3B is frontal view of the rotating magnet B-H meter of the present invention. In the preferred embodiment, the cross-section of the sample holders 11 and 12 is rectangular. This configuration for the sample holders improves the uniformity of the magnetic field over the sample holder region. However, sample holders having a different cross-sectional geometry, (e.g., circular) can be used.

It will be now appreciated that there has been presented apparatus and method for measuring the saturation flux density of a sample medium. It will be clear that the sample holder can be tube and that the medium can flow continuously through the tube. In this manner, the present apparatus can be used to monitor continuously the fluid flowing through the sample holder and can be incorporated as part of a process control system. In the process control system, the concentration of magnetic particles can be continuously monitored and appropriate adjustments performed as a result of the measurements. When a reference material having the desired magnetic properties flows through the reference material sample holder, then the properties of the material being tested can be adjusted with a zero signal applied to the input terminals of the amplifier/meter being the equilibrium signal.

Operation of the present invention is believed to be apparent from the foregoing description and drawings, but a few words will be added for emphasis. The disclosed apparatus is particularly useful in the determination of the properties of materials into which magnetic particles have been dispersed. The disposed apparatus uses relatively simple and relatively inexpensive apparatus while providing an accurate measurement of the saturation flux density.

While the invention has been described with reference to a fluid medium, it is apparent that the invention is easily adapted to the insertion of any magnetic material in the sample holder.

While the invention has been described with particular reference to a preferred embodiment, it will be understood by those skilled in the art that various changes may be made and equivalents may be substituted for elements of the preferred embodiment without departing from invention. In addition, many modifications may be made to adapt a particular situation and material to a teaching of the invention without departing from the essential teachings of the present invention.

As is evident from the foregoing description, certain aspects of the invention are not limited to the particular details of the examples illustrated, and it is therefore contemplated that other modifications and applications will occur to those skilled in the art. It is accordingly intended that the claims shall cover all such modifications and applications as do not depart from the true spirit and scope of the invention.

PARTS LIST 11 first sample holder
12 second sample holder
13 cylindrical permanent magnet 13A direction of magnetization of the permanent magnet 14A axis of rotation of the permanent magnet 14B direction of rotation of the permanent magnet 16 coil surrounding the first sample holder 17 coil surrounding the second sample holder 19 amplifier/meter

What is claim is:

1. A device for measuring the magnetic properties of a material, said device comprising:

a radially magnetized, cylindrical dipole permanent magnet having a rotational axis and having an axis of magnetization perpendicular to and passing through said cylindrical axis;

rotational apparatus for rotating said magnet about a rotational axis;

a first sample holder having a first inductive pick-up coil, said first sample holder positioned on a first side of said magnet, said first sample holder having an axis in a plane perpendicular to said rotational axis; and a second sample holder with a second inductive pickup coil, said second sample holder having a generally symmetric position relative to said first sample holder and said first coil to said first sample holder on said first side of said rotational axis, said coils being electrically coupled to provide a cancellation of signals induced in said pick-up coils as a result of said rotating magnet when no material to be tested is present, wherein said material to be tested being inserted in said first sample holder resulting in an output signal.

2. The device of claim 1 wherein said material to be tested is placed in said first sample holder and produces a signal in said first coil proportional to a time rate of change of magnetic flux produced by said material to be tested.

3. The device of claim 2 wherein said first and said second sample holders have an arcuate portion which is generally equidistant from an axis of said cylindrical magnet.

4. The device of claim 1 wherein said material to be tested is a fluid, said fluid flowing through said first sample holder.

5. The device of claim 4 wherein a reference fluid material flows through said second sample holder.

6. The device of claim 1 wherein said first and said second sample holders have a rectangular cross-section.

7. A method of determining magnetic properties of a material, said method comprising the steps of:

placing said material in a first sample holder associated with a first inductive pick-up coil;

positioning a rotating cylindrical dipole permanent magnet in a position proximate said first inductive pick-up coil wherein said magnet has a rotational axis and has an axis of magnetization perpendicular to and passing through said cylindrical axis;

positioning a second sample holder associated with a second inductive pick-up coil in a symmetrical position relative to said first sample holder and said first inductive pick-up coil on a same side of said rotating cylindrical magnet as said first inductive pick-up coil; and electrically coupling said first and said second inductive pick-up coil to provide a substantially null signal in the absence of said material.

8. The method of claim 7 further including the step of selecting said second inductive pick-up coil to be substantially identical to said first pick-up coil and having second sample holder associated therewith.

9. The method of claim 8 wherein said material is a fluid, said method further including the step of flowing said fluid through said first sample holder.

10. The method of claim 9 further comprising the step of flowing a reference fluid through said second sample holder.

11. The method of claim 10 wherein said first and second sample holders have a rectangular cross-section.

12. Apparatus for measuring at least one magnetic parameter of a material, said apparatus comprising:

a first coil surrounding a first sample holder;

a cylindrical dipole permanent magnet having an axis of rotation and polarized perpendicularly to the axis of said cylindrical permanent magnet with an axis of magnetization perpendicular to and passing through said axis of rotation, wherein said first coil has an axis in a plane perpendicular to said permanent magnet axis;

a second coil generally identical to said first coil and positioned on the same side of said permanent magnet as said first coil, said first and said second coil being generally symmetric relative to one another and with respect to said permanent magnet; and apparatus for rotating said cylindrical permanent magnet about said permanent magnetic axis, wherein said first and said second coils are electrically coupled to provide a zero output voltage when a sample of said material is not in said first sample holder.

13. The apparatus of claim 12 wherein said material is a fluid, said first sample holder being a first tube through which said fluid flows.

14. The apparatus of claim 13 further comprising a second sample holder associated with said second coil, said second sample holder being a second tube.

15. The apparatus of claim 14 wherein a reference fluid flows through said second sample holder.

16. The apparatus of claim 15 wherein said first and said second tubes have an arcuate portion which is equidistant from said axis of cylindrical permanent magnet.

17. The apparatus of claim 16 wherein said first and said second tubes have a rectangular cross-section.

* * * * *